United States Patent [19]

Okabe et al.

[11] 4,320,126
[45] Mar. 16, 1982

[54] TRIAZINYL-ORGANOPHOSPHORUS ESTERS

[75] Inventors: Takayuki Okabe, Nishinomiya; Kunio Mukai, Takarazuka; Masachika Hirano, Ibaraki, all of Japan

[73] Assignee: Sumitomo Chemical Company, Limited, Osaka, Japan

[21] Appl. No.: 70,056

[22] Filed: Aug. 27, 1979

[30] Foreign Application Priority Data

Sep. 4, 1978 [JP] Japan .............................. 53-108779

[51] Int. Cl.³ .................... C07D 251/34; A01N 43/66
[52] U.S. Cl. ..................................... 424/249; 544/214
[58] Field of Search ........................ 544/214; 424/249

[56] References Cited

U.S. PATENT DOCUMENTS

| | | | |
|---|---|---|---|
| 2,980,675 | 4/1961 | Schwarze | 544/214 |
| 3,261,834 | 7/1966 | Imel et al. | 544/214 |
| 4,038,197 | 7/1977 | Caspari | 544/214 |

FOREIGN PATENT DOCUMENTS

| | | |
|---|---|---|
| 713278 | 8/1954 | United Kingdom. |
| 993813 | 6/1965 | United Kingdom. |
| 1087029 | 10/1967 | United Kingdom. |

OTHER PUBLICATIONS

Slotta et al., *Berichte*, vol. 60, pp. 301–304 (1927).

*Primary Examiner*—John M. Ford
*Attorney, Agent, or Firm*—Stevens, Davis, Miller & Mosher

[57] ABSTRACT

Organophosphorus esters of the formula (I),

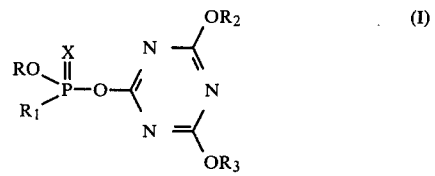

wherein R is a $C_1$–$C_2$ alkyl group, $R_1$ is a $C_1$–$C_2$ alkyl, $C_1$–$C_2$ alkoxy, $C_1$–$C_4$ alkylamino, phenyl or phenoxy group, $R_2$ and $R_3$, which may be the same or different, are each a $C_1$–$C_5$ alkyl or methoxy $C_2$–$C_3$ alkyl group and X is an oxygen or sulfur atom, a method for producing organophosphorus esters of the formula (I) characterized by condensation reaction of s-triazines of the formula,

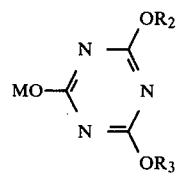

wherein M is a potassium or sodium atom and $R_2$ and $R_3$ are as defined above, with a halogenated compound of the formula,

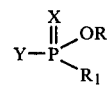

wherein Y is a halogen atom and R, $R_1$ and X are as defined above, and an insecticide, acaricide and/or nematocide characterized by containing organophosphorus esters of the formula (I) as an active ingredient.

8 Claims, No Drawings

TRIAZINYL-ORGANOPHOSPHORUS ESTERS

The present invention relates to novel organophosphorus esters, their production and an insecticide, acaricide and/or nematocide characterized by containing them as an active ingredient.

More particularly, the present invention relates to (1) organophosphorus esters of the formula (I),

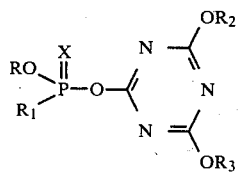

wherein R is a $C_1$–$C_2$ alkyl group, $R_1$ is a $C_1$–$C_2$ alkyl, $C_1$–$C_2$ alkoxy, $C_1$–$C_4$ alkylamino, phenyl or phenoxy group, $R_2$ and $R_3$, which may be the same or different, are each a $C_1$–$C_5$ alkyl or methoxy $C_2$–$C_3$ alkyl group and X is an oxygen or sulfur atom, (2) a method for producing organophosphorus esters of the formula (I) characterized by the condensation reaction of s-triazines of the formula (II),

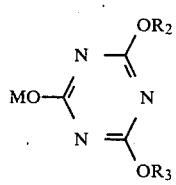

wherein $R_2$ and $R_3$ are as defined above, and M is a potassium or sodium atom, preferably a potassium atom, with a halogenated compound of the formula (III),

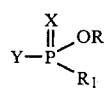

wherein R, $R_1$ and X are as defined above, and Y is a halogen atom (chlorine, bromine, fluorine and iodine), and (3) an insecticide, acaricide and/or nematocide characterized by containing organophosphorus esters of the formula (I),

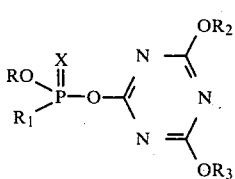

wherein R, $R_1$, $R_2$, $R_3$ and X are as defined above, as an active ingredient.

The compounds of the present invention represented by the formula (I) are novel compounds, and some examples of the compounds will be shown hereinafter. But the present invention is not of course limited to these examples.

| Compound No. | Chemical structure | Physical constant |
|---|---|---|
| (1) | CH$_3$O—[triazine]—OP(OC$_2$H$_5$)$_2$, S= | $n_D^{25.0}$ 1.5011 |
| (2) | CH$_3$O—[triazine]—OP(S)(OC$_2$H$_5$)(O-phenyl) | $n_D^{20.0}$ 1.4824 |
| (3) | CH$_3$O—[triazine]—OP(S)(OC$_2$H$_5$)(phenyl) | $n_D^{21.7}$ 1.4670 |
| (4) | CH$_3$O—[triazine]—OP(S)(OC$_2$H$_5$)(NHCH(CH$_3$)$_2$) | $n_D^{21.0}$ 1.5167 |
| (5) | C$_2$H$_5$O—[triazine]—OP(OC$_2$H$_5$)$_2$, S= | $n_D^{19.0}$ 1.4972 |
| (6) | C$_2$H$_5$O—[triazine]—OP(S)(OC$_2$H$_5$)(O-phenyl) | $n_D^{20.0}$ 1.5582 |
| (7) | C$_2$H$_5$O—[triazine]—OP(S)(OC$_2$H$_5$)(phenyl) | $n_D^{20.0}$ 1.5455 |
| (8) | C$_2$H$_5$O—[triazine]—OP(S)(OC$_2$H$_5$)(NHCH(CH$_3$)$_2$) | $n_D^{20.0}$ 1.5030 |
| (9) | n-C$_3$H$_7$O—[triazine]—OP(S)(OC$_2$H$_5$)(NHC$_4$H$_9$(n)) | $n_D^{25.5}$ 1.4970 |

| Compound No. | Chemical structure | Physical constant |
|---|---|---|
| (10) | n-C$_3$H$_7$O—C(=N)—N=C(On-C$_3$H$_7$)—N—OP(=S)(NHC$_4$H$_9$(iso))(OC$_2$H$_5$) | $n_D^{25.5}$ 1.4977 |
| (11) | n-C$_3$H$_7$O—C(=N)—N=C(On-C$_3$H$_7$)—N—OP(=S)(NHC$_4$H$_9$(sec))(OC$_2$H$_5$) | $n_D^{25.5}$ 1.4968 |
| (12) | n-C$_3$H$_7$O—C(=N)—N=C(On-C$_3$H$_7$)—N—OP(=S)(OCH$_3$)$_2$ | $n_D^{21.5}$ 1.4996 |
| (13) | n-C$_3$H$_7$O—C(=N)—N=C(On-C$_3$H$_7$)—N—OP(=S)(OC$_2$H$_5$)$_2$ | $n_D^{21.5}$ 1.4920 |
| (14) | n-C$_3$H$_7$O—C(=N)—N=C(On-C$_3$H$_7$)—N—OP(=S)(C$_6$H$_5$)(OC$_2$H$_5$) | $n_D^{21.5}$ 1.5420 |
| (15) | n-C$_3$H$_7$O—C(=N)—N=C(On-C$_3$H$_7$)—N—OP(=S)(OC$_6$H$_5$)(OC$_2$H$_5$) | $n_D^{21.5}$ 1.5162 |
| (16) | iso-C$_3$H$_7$O—C(=N)—N=C(Oiso-C$_3$H$_7$)—N—OP(=S)(OCH$_3$)$_2$ | $n_D^{23.0}$ 1.4940 |
| (17) | iso-C$_3$H$_7$O—C(=N)—N=C(Oiso-C$_3$H$_7$)—N—OP(=S)(OC$_2$H$_5$)$_2$ | $n_D^{23.0}$ 1.4900 |
| (18) | iso-C$_3$H$_7$O—C(=N)—N=C(Oiso-C$_3$H$_7$)—N—OP(=S)(C$_6$H$_5$)(OC$_2$H$_5$) | $n_D^{22.5}$ 1.5410 |
| (19) | iso-C$_3$H$_7$O—C(=N)—N=C(Oiso-C$_3$H$_7$)—N—OP(=S)(OC$_6$H$_5$)(OC$_2$H$_5$) | $n_D^{26.0}$ 1.5165 |
| (20) | iso-C$_3$H$_7$O—C(=N)—N=C(Oiso-C$_3$H$_7$)—N—OP(=S)(NHCH$_3$)(OCH$_3$) | $n_D^{24.5}$ 1.5109 |
| (21) | iso-C$_3$H$_7$O—C(=N)—N=C(Oiso-C$_3$H$_7$)—N—OP(=S)(NHC$_2$H$_5$)(OCH$_3$) | $n_D^{23.5}$ 1.5065 |
| (22) | iso-C$_3$H$_7$O—C(=N)—N=C(Oiso-C$_3$H$_7$)—N—OP(=S)(NHCH$_3$)(OC$_2$H$_5$) | $n_D^{23.5}$ 1.5068 |
| (23) | iso-C$_3$H$_7$O—C(=N)—N=C(Oiso-C$_3$H$_7$)—N—OP(=S)(NHC$_2$H$_5$)(OC$_2$H$_5$) | $n_D^{22.0}$ 1.4991 |
| (24) | iso-C$_3$H$_7$O—C(=N)—N=C(Oiso-C$_3$H$_7$)—N—OP(=S)(NHCH(CH$_3$)$_2$)(OC$_2$H$_5$) | $n_D^{22.0}$ 1.4945 |
| (25) | iso-C$_3$H$_7$O—C(=N)—N=C(Oiso-C$_3$H$_7$)—N—OP(=S)(NHC$_4$H$_9$(n))(OC$_2$H$_5$) | $n_D^{25.5}$ 1.4975 |
| (26) | iso-C$_3$H$_7$O—C(=N)—N=C(Oiso-C$_3$H$_7$)—N—OP(=S)(C$_2$H$_5$)(OC$_2$H$_5$) | $n_D^{23.5}$ 1.5085 |
| (27) | n-C$_4$H$_9$O—C(=N)—N=C(On-C$_4$H$_9$)—N—OP(=S)(OCH$_3$)$_2$ | $n_D^{21.0}$ 1.4968 |

-continued

| Compound No. | Chemical structure | Physical constant |
|---|---|---|
| (28) | n-C4H9O, N, n-C4H9O — triazine — OP(S)(OC2H5)2 | $n_D^{23.0}$ 1.4845 |
| (29) | n-C4H9O, N, n-C4H9O — triazine — OP(S)(C6H5)(OC2H5) | $n_D^{20.0}$ 1.5281 |
| (30) | iso-C4H9O, N, iso-C4H9O — triazine — OP(S)(OC2H5)2 | $n_D^{26.0}$ 1.4840 |
| (31) | iso-C4H9O, N, iso-C4H9O — triazine — OP(S)(C6H5)(OC2H5) | $n_D^{24.0}$ 1.5293 |
| (32) | sec-C4H9O, N, sec-C4H9O — triazine — OP(S)(OC2H5)2 | $n_D^{22.0}$ 1.4601 |
| (33) | n-C5H11O, N, n-C5H11O — triazine — OP(S)(OC2H5)2 | $n_D^{26.0}$ 1.4723 |
| (34) | n-C5H11O, N, n-C5H11O — triazine — OP(S)(C6H5)(OC2H5) | $n_D^{26.0}$ 1.5220 |
| (35) | iso-C5H11O, N, iso-C5H11O — triazine — OP(S)(OC2H5)2 | $n_D^{26.0}$ 1.4770 |
| (36) | iso-C5H11O, N, iso-C5H11O — triazine — OP(S)(C6H5)(OC2H5) | $n_D^{26.0}$ 1.5127 |
| (37) | CH3OCH2CH2O, N, CH3OCH2CH2O — triazine — OP(S)(OC2H5)2 | $n_D^{24.5}$ 1.4954 |
| (38) | CH3OCH2CH2O, N, CH3OCH2CH2O — triazine — OP(S)(C6H5)(OC2H5) | $n_D^{27.0}$ 1.5421 |
| (39) | CH3OCH2CH(CH3)O, N, CH3OCH2CH(CH3)O — triazine — OP(S)(OC2H5)2 | $n_D^{24.5}$ 1.4902 |
| (40) | C2H5O, N, C2H5O — triazine — OP(O)(OC2H5)2 | $n_D^{29.0}$ 1.4640 |
| (41) | iso-C3H7O, N, iso-C3H7O — triazine — OP(O)(OC2H5)2 | $n_D^{29.0}$ 1.4593 |

The compounds of the present invention can be obtained with satisfactory results by reacting s-triazines (II) with a halogenated compound (III) in an amount of 0.9 to 1.0 time by mole based on the s-triazines at a temperature of from about 0° C. to about 100° C. for 1 to 10 hours with stirring in a solvent and if necessary in the presence of 0.1 to 10 mole % of copper powder, cuprous chloride or a phase transfer catalyst (e.g. quaternary ammonium salts, phosphonium salts, crown ethers). The solvent includes for example ketones (e.g. acetone, methyl isobutyl ketone), acetonitrile, benzene, toluene and water. After completion of the reaction, the objective compounds can be isolated by the usual after-treatments, and if necessary they may further be purified by distillation or chromatography on silica gel.

Some examples of s-triazines and halogenated compounds, starting materials of the present compounds, will be shown hereinafter.

s-Triazines:

| | |
|---|---|
| Potassium 2,4-dimethoxy-s-triazin-6-olate | (known compound) |
| Potassium 2,4-diethoxy-s-triazin-6-olate | (novel compound but its free acid is known) |
| Potassium 2,4-di-n-propoxy-s-triazin-6-olate | (novel compound but its free acid is known) |
| Potassium 2,4-di-isopropoxy-s- | |

-continued

| s-Triazines: | |
|---|---|
| triazin-6-olate | (novel compound) |
| Potassium 2,4-di-n-butoxy-s-triazin-6-olate | (novel compound) |
| Potassium 2,4-di-isobutoxy-s-triazin-6-olate | (novel compound) |
| Potassium 2,4-di-sec-butoxy-s-triazin-6-olate | (novel compound) |
| Potassium 2,4-di-n-pentyloxy-s-triazin-6-olate | (novel compound) |
| Potassium 2,4-di-isopentyloxy-s-trizin-6-olate | (novel compound) |
| Potassium 2,4-bis(methoxyethoxy)-s-triazin-6-olate | (novel compound) |
| Potassium 2,4-bis($\beta$-methoxy-isopropoxy)-s-triazin-6-olate | (novel compound) |
| Sodium 2,4-bis($\beta$-methoxy-isopropoxy)-s-triazin-6-olate | (novel compound) |
| Potassium 2,4-bis(allyloxy)-s-triazin-6-olate | (novel compound) |

Halogenated compound:
Ethyl phenylphosphonochloridothionate
O,O-dimethyl phosphorochloridothionate
O,O-diethyl phosphorochloridothionate
O-ethyl O-phenylphosphorochloridothionate
O-methyl N-methylphosphoramidochloridothionate
O-methyl N-ethylphosphoramidochloridothionate
O-methyl N-n-propylphosphoramidochloridothionate
O-methyl N-isopropylphosphoramidochloridothionate
O-methyl N-n-butylphosphoramidochloridothionate
O-methyl N-isobutylphosphoramidochloridothionate
O-methyl N-sec-butylphosphoramidochloridothionate
O-ethyl N-methylphosphoramidochloridothionate
O-ethyl N-ethylphosphoramidochloridothionate
O-ethyl N-n-propylphosphoramidochloridothionate
O-ethyl N-isopropylphosphoramidochloridothionate
O-ethyl N-n-butylphosphoramidochloridothionate
O-ethyl N-isobutylphosphoramidochloridothionate
O-ethyl N-sec-butylphosphoramidochloridothionate
O,O-dimethyl phosphorochloridate
O,O-diethyl phosphorochloridate
O,O-diethyl phosphorobromidate The halogenated compounds described above can by synthesized by the methods disclosed in the following literatures:

K. Sasse, Organische Phosphorverbindungen, in Methoden der Organischen Chemie, Vol XII/1. Müller, Ed., Georg Thieme Verlag, Stuttgart, 1963

K. Sasse, Organische Phosphorverbindungen, in Methoden der Organischen Chemie, Vol XII/2. Müller, Ed., Georg Thieme Verlag, Stuttgart, 1964

Insecticides, acaricides and nematocides have made a great contribution to remarkably increase agricultural production through their controlling effects against various harmful insects parasitic on agricultural crops. However, various problems such as toxicity to mammals and pollution of natural environment have appeared to develop to such a degree that the use of effective insecticides, acaricides and nematocides is feared in some fields.

For the reasons as described above, there is a strong demand for the development of insecticides, acaricides and nematocides which are low in toxicity, free from fear of environmental pollution and effective in controlling harmful insects.

As a result of extensive study to develop excellent insecticides, acaricides and nematocides satisfying the above requirements, the inventors found that the present compounds of the formula (I) have properties meeting the above requirements, and thus completed the present invention. The present compounds of the formula (I) are particularly suitable for controlling stemborers, planthoppers, leafhoppers and bugs in paddy field; insects doing damage to vegetables, fruit trees and wood, for example insects belonging to Lepidoptera [e.g. diamondback moth (*Plutella xylostella*), armyworms and cutworms, tortorixes] and Orthoptera (e.g. grasshoppers); mites, nematodes and disease-carrying mosquitoes, flies, cockroaches, ticks, fleas and lice; and insects harmful to stored cereals.

In the practical application of the present compounds, they may be applied alone without other components or in mixtures with carriers for ease of use as controlling agents. The commonly used preparation forms, for example emulsifiable concentrates, wettable powders, dusts, granules, fine granules, oil sprays, aerosols and baits, can be produced optionally, with no need of particular conditions, by the methods well known to those skilled in the art according to the methods for producing common agricultural chemicals. The compounds of the present invention can be applied to various usages in required preparation forms and with required carriers. The foregoing preparations generally contain 0.1 to 95% by weight of active ingredient (including other ingredients mixed).

Further, multi-purpose compositions of excellent efficacy can be produced by mixing with other active ingredients, for example, organo-phosphorus insecticides such as O,O-dimethyl O-(3-methyl-4-nitrophenyl)phosphorothioate (hereinafter referred to as Sumithion, a registered trade mark of Sumitomo Chemical Co.) and O,O-dimethyl O-(2,2-dichlorovinyl)phosphate (hereinafter referred to as DDVP); carbamate insecticides such as 1-naphthyl N-methylcarbamate, 3,4-dimethylphenyl N-methylcarbamate and 3,5-dimethylphenyl N-methylcarbamate; Allethrin, 3,4,5,6-tetrahydrophthalimidomethyl chrysanthemate (hereinafter referred to as tetramethrin), 5-benzyl-3-furylmethyl chrysanthemate (hereinafter referred to as Chrysron, a registered trade mark of Sumitomo Chemical Co.); other insecticides such as B.T., fungicides, nematocides, acaricides, herbicides, insect hormone compounds, other agricultural chemicals and fertilizers. Further, a synergistic effect can be expected by such mixing.

The present invention will be illustrated in more detail with reference to the following examples and preparation examples.

EXAMPLE 1

(Compound No. 1)

O,O-diethyl phosphorochloridothionate (1.89 g, 0.01 mole) was added dropwise, at room temperature with stirring, to a suspension of potassium 2,4-dimethoxy-s-triazin-6-olate (1.91 g, 0.01 mole) in acetone (30 ml). The mixture was heated under reflux for 1 hr with stirring and then cooled to room temperature. The reaction mixture was poured into benzene (150 ml), and the benzene solution was washed with 5% aqueous sodium hydroxide solution and then with water. The benzene layer was dried over anhydrous sodium sulfate and concentrated under reduced pressure to yield 2.3 g of a pale yellow oily residue. The residue was purified by column chromatography of silica gel to obtain 1.8 g of O,O-diethyl O-(2,4-dimethoxy-s-triazin-6-yl)phosphorothionate as a colorless, transparent oil. Refractive index $n_D^{25.0}$ 1,5011

| Elementary analysis: | | | |
| --- | --- | --- | --- |
| | C(%) | H(%) | N(%) |
| Calcd. for $C_7H_{12}N_3O_5PS$: | 29.89 | 4.27 | 14.95 |
| Found: | 29.61 | 4.47 | 14.72 |

EXAMPLE 2

(Compound No. 8)

O-ethyl N-isopropylphosphoramidochloridothionate (2.00 g, 0.01 mole) was added dropwise, at room temperature with stirring, to a suspension of potassium 2,4-diethoxy-s-triazin-6-olate (2.23 g, 0.01 mole) in acetone (50 ml). The mixture was heated under reflux for 1.5 hr with stirring. The reaction mixture was cooled to room temperature and poured into toluene (200 ml). The toluene solution was washed with water, and the toluene layer was dried over anhydrous sodium sulfate and concentrated under reduced pressure to yield 2.0 g of a pale yellow oily residue. The residue was purified by column chromatography on silica gel to give 1.6 g of O-ethyl O-(2,4-diethoxy-s-triazin-6-yl) N-isopropyl phosphoramidothionate as a pale yellow oil. Refractive index $n_D^{20.0}$ 1.5030

| Elementary analysis: | | | |
| --- | --- | --- | --- |
| | C(%) | H(%) | N(%) |
| Calcd. for $C_{12}H_{23}N_4O_4PS$: | 41.14 | 6.57 | 16.00 |
| Found: | 41.51 | 6.42 | 16.36 |

Compounds No. 2 to No. 7 and No. 9 to No. 37 were synthesized in the same manner as above.

Potassium 2,4-dialkoxy-s-triazin-6-olate, a starting material, was synthesized according to the method disclosed in K. H. Slotta et al., Chem. Ber., 60, 303 (1927).

REFERENCE EXAMPLE 1

Cyanuric chloride (30.0 g, 0.163 mole) was dissolved in isopropyl alcohol (180 ml), to which powdered sodium hydroxide (19.52 g, 0.488 mole) was added thereto at 25° to 30° C. over 30 minutes with stirring. The resulting white suspension was stirred at 30° C. for 2 hours and then at 40° C. for 1 hour, and filtered. The precipitated sodium chloride was washed with three 50-ml portions of isopropyl alcohol, and the filtrate and washings were combined. The powdered potassium hydroxide (9.13 g, 0.163 mole) was added to the mixture. The mixture was refluxed for 1 hour with stirring and concentrated under reduced pressure to yield white crystals. The crystals were washed with cold isopropyl alcohol and then with ether to obtain 37.6 g of potassium 4,6-dipropoxy-s-triazin-2-olate as white crystals. Melting point 235°–236° C.

PREPARATION EXAMPLE 1

Fifty parts of each of the present compounds (1) to (41) are dissolved in 40 parts of xylene, to which 10 parts of Sorpol SM-200, an emulsifier, (a registered trade mark of Toho Kagaku Co., a mixture of an anionic surfactant and a nonionic one) are added. The mixture is thoroughly stirred to obtain an emulsifiable concentrate of each compound.

PREPARATION EXAMPLE 2

Twenty parts of Sumithion (described hereinbefore) are added to 20 parts of each of the present compounds (1), (2), (3), (5), (12) and (27), to which 50 parts of xylene and 10 parts of Sorpol SM-200 (described above) are added. The mixture is thoroughly stirred to obtain an emulsifiable concentrate.

PREPARATION EXAMPLE 3

Forty parts of each of the present compounds (1) to (41) are well mixed with 5 parts of Sorpol SM-200 (described above), to which 55 parts of 300-mesh diatomaceous earth is added. The mixture is well mixed by a mortar to obtain a wettable powder of each compound.

PREPARATION EXAMPLE 4

Three parts of each of the present compounds (1) to (41) are dissolved in 20 parts of acetone, to which 97 parts of 300-mesh talc is added. The mixture is thoroughly mixed by a mortar, and acetone is then removed by evaporation to obtain a dust of each compound.

PREPARATION EXAMPLE 5

Two parts of 3-methylphenyl N-methylcarbamate are added to 2 parts of each of the present compounds (6), (14), (16) and (29), and the mixture is dissolved in 20 parts of acetone. After adding 96 parts of 300-mesh talc thereto, the mixture is treated in the same manner as in Preparation example 4 to obtain a dust.

PREPARATION EXAMPLE 6

To 3 parts of each of the present compounds (1) to (41) are added 5 parts of Toyolignin CT (sodium lignosulfonate, a registered trade mark of Toyo Spinning Co.) and 92 parts of GSM Clay (a registered trade mark of Zieklite Mining Co.), and the mixture is well mixed by a mortar. Thereafter, the mixture is well mixed with water in an amount of 10% based thereon, granulated by means of a granulator and air dried to obtain a granule of each compound.

PREPARATION EXAMPLE 7

To 3 parts of each of the present compounds (1) to (41) are added 5 parts of Toyolignin CT (described above) and 92 parts of GSM Clay (described above), and the mixture is well mixed by a mortar. Thereafter, the mixture is well mixed with water in an amount of 10% based thereon, granulated by means of a granulator for fine granule production and air dried to obtain a fine granule of each compound.

PREPARATION EXAMPLE 8

0.2 Part of each of the present compounds (1) and (41) are dissolved in kerosene and made up to 100 parts with kerosene to obtain an oil spray.

PREPARATION EXAMPLE 9

A mixture of 0.2 part of the present compound (17) and 0.1 part of tetramethrin is dissolved in kerosene and made up to 100 parts with kerosene to obtain an oil spray.

PREPARATION EXAMPLE 10

0.2 Part of the present compound (6), 0.2 part of (+)-trans-allethrin, 7 parts of xylene and 7.6 parts of deodorized kerosene are well mixed to make a solution. The solution is filled in an aerosol container. After attaching a valve portion to the container, 85 parts of a propellant (liquefied petroleum gas) are charged therein under pressure through the valve to obtain an aerosol.

PREPARATION EXAMPLE 11

0.2 Part of the present compound (29), 0.1 part of tetramethrin, 11.7 parts of deodorized kerosene and 1 part of Atmos 300, an emulsifier, (a registered trade mark of Atlas Chemical Co., monoglyceride series emulsifier) are mixed, and then emulsified with addition of 50 parts of distilled water. The emulsion is then filled in an aerosol container together with 37 parts of a 3:1 mixture of deodorized butane and deodorized propane to obtain a water-based aerosol.

EXAMPLE 3

The emulsifiable concentrate obtained in Preparation example 1 was diluted 1000 times with water (corresponding to 500 ppm of the active ingredient). On the bottom of a polyethylene cup of 5.5 cm in diameter was placed a piece of filter paper of the same size, and 0.7 ml of the above diluted liquor was dropped on the filter paper. Sucrose (30 mg) was placed on the paper as diet. Thereafter, 10 housefly female adults (*Musca domestica*) were liberated in the cup which was then covered with a lid. After 48 hours, the dead and alive were counted to obtain mortality.

| Test compound | Mortality (%) | Test compound | Mortality (%) |
|---|---|---|---|
| (1) | 100 | (22) | 100 |
| (2) | 100 | (23) | 100 |
| (3) | 100 | (24) | 100 |
| (4) | 100 | (25) | 100 |
| (5) | 100 | (27) | 100 |
| (6) | 100 | (28) | 100 |
| (7) | 100 | (29) | 95 |
| (8) | 100 | (30) | 95 |
| (9) | 100 | (31) | 100 |
| (10) | 100 | (32) | 100 |
| (11) | 100 | (33) | 100 |
| (12) | 100 | (34) | 100 |
| (13) | 100 | (36) | 100 |
| (14) | 100 | (37) | 100 |
| (15) | 100 | (38) | 100 |
| (16) | 100 | (39) | 100 |
| (17) | 100 | (40) | 100 |
| (18) | 100 | (41) | 100 |
| (19) | 100 | No treatment | 0 |
| (20) | 100 | | |
| (21) | 100 | | |

EXAMPLE 4

Of the emulsifiable concentrates obtained in Preparation example 1, those containing the present compounds (5), (8), (13), (17) and (32) were diluted 1000 times with water. The diluted liquor was sprayed on rice plants cultivated in a Wagner's pot at a rate of 15 ml per pot. After air-drying, the pot was covered with a wire cage, and 15 smaller brown planthopper adults (*Laodelphax striatellus*) were liberated therein. In order to examine the residual effect, another group of 15 smaller brown planthopper adults were liberated therein 5 days after spraying. The dead and alive of each group were counted 24 hours after the group was liberated in the cage. The mortality is shown in the following table (2 replications).

| Test compound | Liberation on the spraying day | Liberation 5 days after spraying |
|---|---|---|
| (5) | 100 | 80 |
| (8) | 100 | 73 |
| (13) | 100 | 67 |
| (17) | 100 | 90 |
| (32) | 97 | 70 |
| Diazinon* | 97 | 63 |
| MPMC** | 100 | 50 |
| No treatment | 0 | 3 |

*Control: O,O-diethyl O-(2-isopropyl-4-methyl-6-pyrimidinyl)phosphorothionate
**Control: 3,4-Xylyl-N-methylcarbamate

EXAMPLE 5

Five milliliters of each oil spray obtained in Preparation example 9 were sprayed on about 100 housefly adults (*Musca domestica*) per group, according to the Campbel's turntable method [Soap and Sanitary Chemicals, Vol. 14, No. 6, 119 (1938)]. The housefly adults were exposed to the descending mist for 10 minutes. By the next day, all the houseflies could be killed in each case.

EXAMPLE 6

The insecticidal activity on housefly adults (*Musca domestica*) of each aerosol obtained in Preparation examples 10 to 11 was tested by the aerosol test method (Soap and Chemical Specialities, Blue Book, 1965) using a (6 ft)$^3$ Peet Grady's chamber. As a result, with each aerosol, more than 80% of the flies could be knocked down 15 minutes after spraying, and more than 70% of the flies could be killed by the next day.

EXAMPLE 7

Each dust obtained in Preparation example 5 was applied, by means of a Bell jar duster, on potted rice seedlings (diameter of pot, 10 cm), which had elapsed 20 days after sowing, at a rate of 3 kg/10 ares under a pressure of 200 mmHg. After application, the pot was covered with a wire cage, and about 20 green rice leafhopper adults (*Nephotettix cincticeps*) were liberated therein. After 24 hours, the dead and alive were counted, and it was found that the mortality was 100% in each case.

EXAMPLE 8

Carmine mite female adults (*Tetranychus cinnabarinus*) were made parasitic on the leaves of potted kidney bean (primordial stage), at a rate of 10–15/leaf, which had elapsed 9 days after sowing, and bred at 27° C. for a week in a constant temperature room. Then, numerous carmine mites were found to be bred at various growth stages. At this time, a 1000-fold aqueous dilute liquor of each emulsifiable concentrate obtained in Preparation example 1 was sprayed on the kidney bean at a rate of 10 ml per pot by means of a turn table. Eight days after spraying, the degree of damage of kidney bean and the number of female adults were examined (2 replications).

| Test compound | Degree of damage* | Number of female adults |
|---|---|---|
| (3) | — | 0 |
| (5) | — | 2 |
| (6) | — | 8 |
| (7) | — | 0 |
| (8) | — | 0 |

-continued

| Test compound | Degree of damage* | Number of female adults |
|---|---|---|
| (20) | — | 11 |
| (31) | — | 21 |
| (36) | — | 26 |
| (37) | — | 0 |
| Chlorodimeform** | — to + | 27 |
| No treatment | +++ | 698 |

*The degree of damage was classified as follows:
—: <10%
+: 10–50%
++: 50–90%
+++: >90%
**Control: N'-(2-methyl-4-chlorophenyl)-N,N-dimethylformamidine

EXAMPLE 9

The egg mass just before hatching of rice stem borer (*Chilo suppressalis*) was put on rice plants at the tillering stage cultivated in a Wagner's pot. After 4 days, a granule containing the present compound (17) among granules obtained in Preparation Example 6 was applied thereto at a rate of 3 kg/10 ares. A 3% Diazinon granule as control was applied at the same rate. Five days after application, the rice stem was cut to count the dead and alive of the larvae (2 replications). Water in the pot was maintained 3 cm deep throughout the test period.

| Test compound | Mortality (%) |
|---|---|
| (17) | 100 |
| Diazinon | 96 |
| No treatment | 4 |

EXAMPLE 10

Among emulsifiable concentrates obtained in Preparation example 1, the one containing the present compound (1) was diluted 500 times with water. Thereafter, to 10 ml of the dilute liquor was added 0.5 ml of a liquor containing numerous nematodes (*Panagrellus redivivus*). After 48 hours, the dead and alive were examined by means of a binocular microscope, and it was found that all the nematodes were killed.

What is claimed is:

1. An organophosphorus ester of the formula,

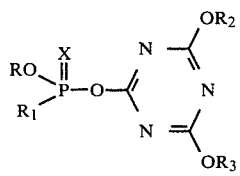

wherein R is a $C_1$–$C_2$ alkyl group, $R_1$ is a $C_1$–$C_2$ alkyl, $C_1$–$C_2$ alkoxy, $C_1$–$C_4$ alkylamino, phenyl or phenoxy group, $R_2$ and $R_3$, which may be the same or different, are each a $C_1$–$C_5$ alkyl or methoxy $C_2$–$C_3$ alkyl group and X is an oxygen or sulfur atom.

2. The compound according to claim 1, wherein both $R_2$ and $R_3$ are an isopropyl group.

3. O,O-Diethyl O-(2,4-diisopropoxy-s-triazin-6-yl)phosphorothionate of the formula,

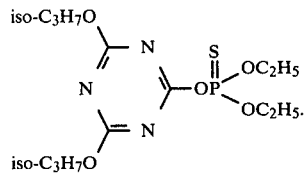

4. O,O-Dimethyl O-(2,4-diisopropoxy-s-triazin-6-yl)phosphorothionate of the formula,

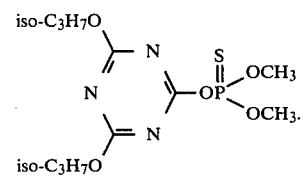

5. O,O-Diethyl O-(2,4-diisopropoxy-s-triazin-6-yl)phosphate of the formula,

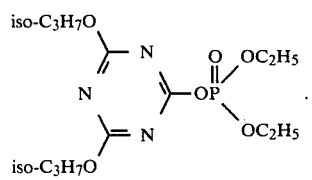

6. O,O-Dimethyl O-(2,4-diisopropoxy-s-triazin-6-yl)phosphate of the formula,

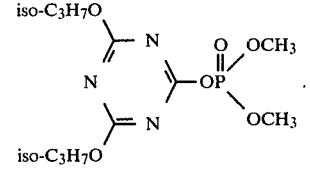

7. An insecticidal, acaricidal or nematocidal composition comprising an inert carrier and as the active ingredient an insecticidally, acaricidally or nematocidally effective amount of a compound according to claim 1.

8. A method for controlling an insect, mite or nematode which comprises contacting the insect, mite or nematode with an insecticidally, acaricidally or nematocidally effective amount of a compound according to claim 1.

* * * * *